(12) United States Patent
Duan

(10) Patent No.: US 11,141,051 B2
(45) Date of Patent: Oct. 12, 2021

(54) ENDOSCOPIC IMAGING APPARATUS, ENDOSCOPIC IMAGING SYSTEM AND METHOD OF USING THE SAME

(71) Applicant: ANKON MEDICALTECHNOLOGIES (SHANGHAI) Co., LTD., Shanghai (CN)

(72) Inventor: Xiaodong Duan, Pleasanton, CA (US)

(73) Assignee: ANKON MEDICAL TECHNOLOGIES (SHANGHAI) CO., LTD.

( * ) Notice: Subject to any disclaimer, the term of this patent is extended or adjusted under 35 U.S.C. 154(b) by 270 days.

(21) Appl. No.: 16/355,663

(22) Filed: Mar. 15, 2019

(65) Prior Publication Data
US 2019/0282076 A1    Sep. 19, 2019

Related U.S. Application Data

(63) Continuation-in-part of application No. 15/922,920, filed on Mar. 16, 2018.

(30) Foreign Application Priority Data

Mar. 11, 2019    (CN) .......................... 201910181949.9

(51) Int. Cl.
*A61B 1/04* (2006.01)
*A61B 1/06* (2006.01)
*A61B 5/06* (2006.01)
*A61B 1/045* (2006.01)
*A61B 1/00* (2006.01)

(52) U.S. Cl.
CPC .......... *A61B 1/041* (2013.01); *A61B 1/00158* (2013.01); *A61B 1/045* (2013.01); *A61B 1/0638* (2013.01); *A61B 5/062* (2013.01)

(58) Field of Classification Search
CPC ........................... A61B 1/041; A61B 1/00158
See application file for complete search history.

(56) References Cited

U.S. PATENT DOCUMENTS

2009/0225157 A1* 9/2009 Orihara .................. A61B 1/041
                                                              348/76
2015/0380140 A1* 12/2015 Duan .................... A61B 1/041
                                                              600/109
2016/0338578 A1* 11/2016 Tearney ............. A61B 1/00128

* cited by examiner

Primary Examiner — Alexandra L Newton
Assistant Examiner — Rynae Boler
(74) Attorney, Agent, or Firm — Treasure IP Group, LLC

(57) ABSTRACT

The present invention discloses an endoscopic imaging apparatus, an endoscopic imaging system and a method of using the same. The endoscopic imaging apparatus includes a diagnostic imaging means, an external control device and an ingestible capsule endoscopy. The external control device positions and/or orientates the capsule endoscopy in a target area. The diagnostic imaging means is included in the capsule endoscopy for diagnostic imaging of a target area under the control of the external control device.

8 Claims, 13 Drawing Sheets

ENDOSCOPIC IMAGING APPARATUS, ENDOSCOPIC IMAGING SYSTEM AND METHOD OF USING THE SAME

CROSS REFERENCE TO RELATED APPLICATIONS

This application claims priority to Chinese Patent Application No. 201910181949.9 filed on Mar. 11, 2019. This application also claim priority in part from the U.S. application Ser. No. 15/922,920, filed on Mar. 15, 2019. The contents of both applications are incorporated by reference herein.

TECHNICAL FIELD

The invention relates to a medical apparatus/system and methods for performing capsule endoscopy and optical biopsy, specifically refers to an endoscopic imaging apparatus, an endoscopic imaging system and method to navigate magnetic capsule endoscope in a human GI track to a target location for performing video endoscopy imaging and oblique back-illumination microscopy (OBM) to diagnose various disease conditions, especially for the early stage cancer in digest channel.

BACKGROUND OF THE INVENTION

Capsule endoscope is a miniaturized camera placed inside a capsule-shaped housing. When a patient swallows such a camera pill, the capsule endoscope travels along the patient's gastrointestinal tract and takes a series of pictures of the interior of the patient gastrointestinal tract. While the capsule endoscope passing through the patient's digestive system, the images taken would be simultaneously transmitted outside of the patient's body to a receiver, and then doctors use the image data for real-time medical examinations.

Capsule endoscope not only has been demonstrated to be very successful in examining patience's interior, but shows clear advantage over traditional endoscope techniques when it comes to examining a patient's small intestine, where the areas or portions of the gastrointestinal tract are not readily accessible by traditional standard endoscopy techniques.

However, studies have shown that the images taken been could only been used as a screening tool. Up to today, the prevalent way to get a more accurate diagnostic for an area of interest in a clinical environment is to perform a biopsy. Generally, a biopsy involves cutting a part of an tissue out from the area of interest, using a device to observe the tissue under high-resolution microscopy, and making an assessment based on morphological considerations. Because biopsy only provides a sparse sampling which is not necessarily be fully representative of the region of interest; and patient always has concerns about the risk of infection relating to tissue biopsies.

Therefore, there is a need to reduce the labor/procedure with the potential risk of the biopsy.

SUMMARY OF THE INVENTION

The present invention discloses an endoscopic imaging apparatus comprising a diagnostic imaging means, an external control device and an ingestible capsule endoscope; wherein the external control device positions and/or orientates the capsule in a target area; the diagnostic imaging means is included in the capsule endoscope for diagnostic imaging of a target area under the control of the external control device.

In one embodiment, the capsule endoscope comprises a capsule shell, a front end and a rear end, and the front end, the rear end and the capsule shell construct an enclosed housing.

In one embodiment, the capsule endoscope further comprises a photographic camera, configured in the enclosed housing for taking image and/or recording video of the target area.

In one embodiment, the capsule endoscope further comprises a first light source for illumination of the target area, configured for working with the photographic camera or the diagnostic imaging means.

In one embodiment, the capsule endoscope further comprises a second light source and/or a third light source for illumination of the target area, configured for working with the diagnostic imaging means or the camera.

In one embodiment, a first light blocking part is configured between the first area at the front end or the rear end corresponding to the diagnostic imaging means and the second area at the front end or the rear end corresponding to the second light source; and a second light blocking part is configured between the first area at the front end or the rear end corresponding to the diagnostic imaging means and the third area at the front end or the rear end corresponding to the third light source.

In one embodiment, the diagnostic imaging means is oblique back illumination microscopy.

In one embodiment, the second source and the third source are used to simultaneously illuminate the diagnostic imaging means with light of the same wavelength or light of the same spectrum, or to separately illuminate the diagnostic imaging means with light of different wavelengths.

The present invention discloses an endoscopic imaging system, operating in a controller of an external control device, wherein the controller comprises a processing unit and a storage medium, program instructions of the endoscopic imaging system are stored in the storage medium and the program instructions is executed by the processing unit to control a capsule endoscope by the following steps: obtain positions of the capsule endoscope and control the capsule endoscope to move to a target area; control the capsule to change orientation; control a diagnostic imaging means to perform diagnostic imaging on the target area.

The present invention discloses an endoscopic imaging method, comprising: an external control device controls a capsule endoscope to move to a target area; the external control device controls the capsule endoscope to change orientation; the external control device controls a diagnostic imaging means to perform diagnostic imaging on the target area.

BRIEF DESCRIPTION OF THE DRAWINGS

In order to more clearly illustrate the embodiments of the present invention or the technical solutions in the prior art, the drawings to be used in the embodiments or the technical description in the prior art will be briefly described below, and obviously, the drawings illustrated below are some embodiments of the present invention, and those skilled in the art can obtain other drawings based on these drawings without any creative work.

The drawings are incorporated in and constitute a part of the specification, which illustrate the embodiments consistent with the present invention and are used in conjunction with the specification to explain the principles of the invention.

DETAILED DESCRIPTION OF THE PREFERRED EMBODIMENTS

Additional embodiments and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

Figure 1:
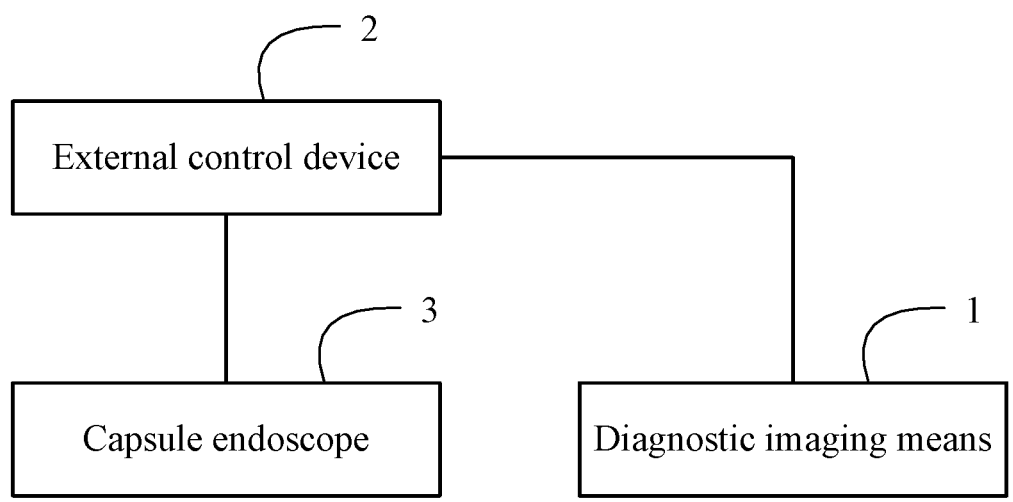
FIG. 1 shows a structural block diagram of an endoscopic imaging apparatus according to an embodiment of the present invention.
Figure 2:
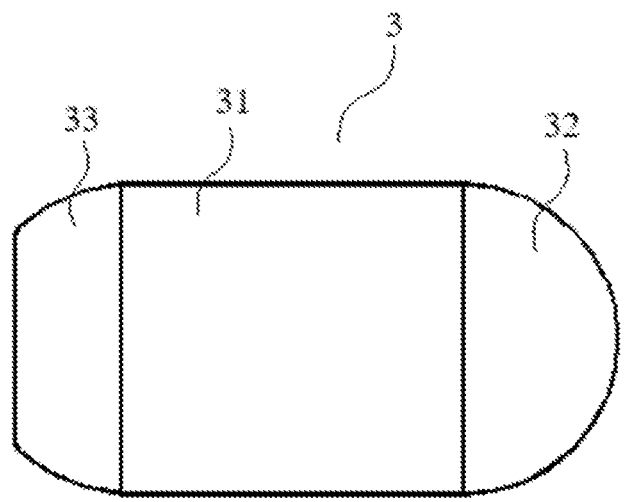
FIG. 2 shows a longitude or a side view of an exemplary capsule endoscope according to one aspect of the present invention.

The structure and method of using an endoscopic imaging apparatus is described in detail below. Elements in the drawings are 1 Diagnostic imaging means
2 External control device
  a. 21 Magnetic ball
3 Capsule endoscope
  a. 31 Capsule shell
  b. 32 Front end
  c. 33 Rear end
    i. 331 First area
    ii. 332 Second area
    iii. 333 Third area
  d. 34 Photographic camera
  e. 35 First light source;
  f. 36 Second light source
  g. 37 Third light source
  h. 38 RF switch
39 Battery
310 Magnet
311 Light blocking ring
  a. 311a First light blocking part
  b. 311b Second light blocking part Referring to FIG. 1, the present invention discloses an endoscopic imaging apparatus, comprising a diagnostic imaging means 1, an external control device 2 and an ingestible capsule endoscope 3. The external control device 2 is configured to position and/or orientate the capsule endoscope 3 in a target area. The diagnostic imaging means 1 is included in the capsule endoscope 3 for diagnostic imaging of the target area under the control of the external control device 2. The diagnostic imaging means to perform optical biopsy in the target area, when a local diseased area is identified. The target area can be a region such as the stomach, small intestine or colon in the digestive tract, in vitro stomach, small intestine or colon, or stomach, small intestine or colon in a digestive tract model.

After a patient takes the capsule endoscope 3, the capsule endoscope 3 can travel through the digestive tract to reach the target area to be examined, and can perform a diagnostic imaging on the target area by the diagnostic imaging means 1. Compared with the prior art, biopsy is not required, thereby improving the accuracy of examination and reducing the risk of infection.

In one embodiment of the present invention, the diagnostic imaging means 1 performs transverse imaging.

In another embodiment of the present invention, the diagnostic imaging means 1 performs cross-sectional imaging.

In one example of the present invention, the diagnostic imaging means 1 performs an imaging depth of 0.1-1 mm below one the surface of the target area.

In another example of the present invention, the diagnostic imaging means 1 has an imaging depth resolution of 5 µm below one surface of the target area.

In the above still another example of the present invention, the diagnostic imaging means 1 has an imaging lateral resolution of 1 um.

Referring to FIGS. 2-7, the capsule endoscope 3 comprises a capsule shell 31, a front end 32 and a rear end 33. The front end 32 and the rear end 33 are respectively fixed at two ends of the capsule shell 31. The front end 32, the rear end 33 and the capsule shell 31 construct an enclosed housing. The capsule endoscope 3 further comprises a magnet 310. The magnet 310 and the diagnostic imaging means 1 are included in the enclosed housing and work in conjunction with the external control device 2. The external control device 2 acts on the magnet 310 to control the capsule endoscope 3 to change its position and orientation.

The magnet 310 can be a permanent magnetic dipole. The permanent magnetic dipole can interact with the external magnetic field of the external control device 2 to move and orientate the capsule endoscope 3. In one embodiment of the present invention, the permanent magnetic dipole has a direction parallel to the length of the capsule endoscope 3.

In order to avoid friction between the capsule endoscope 3 and the patient's digestive tract, which may cause patient discomfort, preferably, the capsule shell 31 is substantially cylindrical shape, the front end 32 is hemi-spherical, and the rear end 33 is truncated hemispherical. The hemispherical front end 32 is the front end of the capsule endoscope 3 while moving in the digestive tract, and the truncated hemispherical rear end 33 is the rear end. The cylindrical portion of the capsule endoscope 3 has a length and a diameter, and the length is the distance between the front end 32 and the rear end 33 in the cylindrical direction. In one embodiment of the present invention, the capsule endoscope 3 has a length less than 30 mm. In one embodiment of the present invention, the capsule endoscope 3 has a diameter less than 10 mm. The capsule endoscope 3 disclosed in the present invention, in one example, has a weight more than 3 g. In another example, the capsule endoscope 3 has a weight less than 10 g. In another example, the capsule endoscope 3 has a weight less than 8 g. In another example, the capsule endoscope 3 has a weight less than 6 g. In another example, the capsule endoscope 3 has a weight less than 5 g.

The capsule endoscope 3 can be controlled by tethered, wireless or tethered and wireless combined method. The capsule endoscope 3 can communicate with the external control device 2 by a wireless method, and be controlled by the external control device 2; or a pulling structure can be provided at the end of the capsule endoscope 3 (for example, a detachable tether is connected to the capsule endoscope 3) to control the capsule endoscope 3.

If the diagnostic imaging means 1 performs diagnostic imaging via the front end 32, preferably, the front end 32 is made of transparent materials. If the diagnostic imaging means 1 performs diagnostic imaging via the rear end 33, preferably, the rear end 33 is made of transparent materials.

Figure 3:
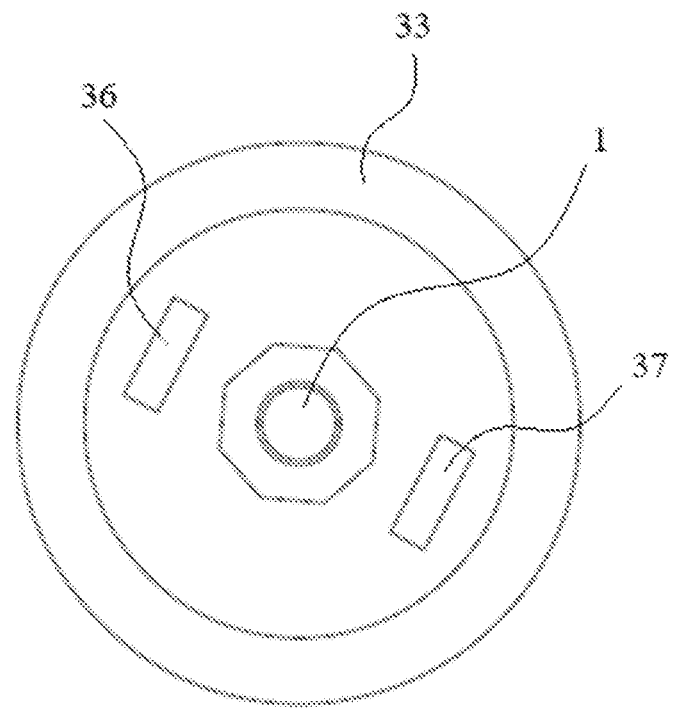
FIG. 3 shows a first cross-sectional view of the exemplary capsule endoscope of FIG. 2, viewing from the left/rear end of the capsule.
Figure 4:
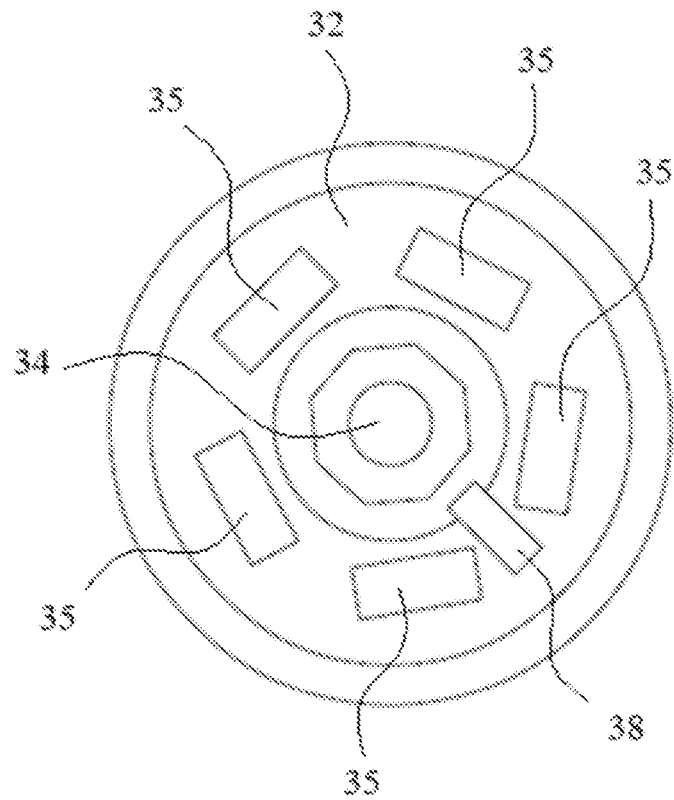
FIG. 4 shows a second cross-sectional view of the exemplary capsule endoscope of FIG. 2, viewing from the right/front end.
Figure 5:
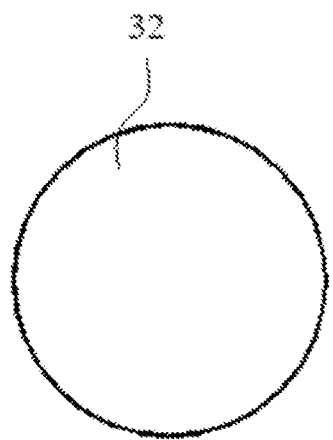
FIG. 5 shows a front end view of the exemplary capsule of FIG. 2.
Figure 6:
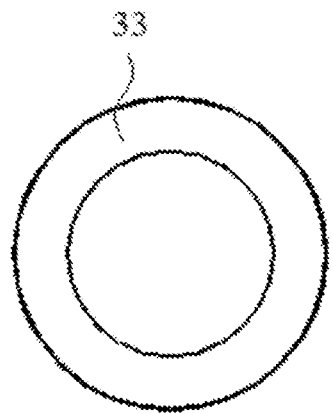
FIG. 6 shows a rear end view of the exemplary capsule of FIG. 2.

Referring to FIGS. 3 and 4, preferably, the capsule endoscope 3 further comprises a first light source 35 to provide illumination for the diagnostic imaging means 1. According to the embodiment of the invention, the preferred is that, the capsule endoscope 3 further comprises a photographic camera 34 configured in the enclosed housing for taking image and/or recording video of the target area. The first light source 35 can also provide illumination for the photographic camera 34.

The capsule endoscope 3 further comprises a second light source 36 and/or a third light source 37 for illuminating the target area for the diagnostic imaging means 1 or the photographic camera 34. It will be understood by those skilled in the art that the quantity of the first light source 35, the second light source 36, and the third light source 37 can each be one or more. In the embodiment, the quantity of the first light sources 35 is five, which are configured around the center of the photographic camera 34, so that the area needs to be illuminated can be lighted up more homogeneously. The quantity of the second light source 36 is one, and the quantity of the third light source 37 is also one, which are symmetrically disposed around the diagnostic imaging device 1.

In addition, the second light source 36 and the third light source 37 are on the same side of the capsule endoscope 3; the first light source 35 is on a side of the capsule endoscope 3 away from the second light source 36 and the third light source 37.

In the embodiment, the diagnostic imaging means 1 can be an OBM (OBLIQUE BACK ILLUMINATION MICROSCOPY). Any of the first light source 35, the second light source 36, and the third light source 37 may be an LED. An RF (Radio Frequency) switch 38 is provided between any two adjacent LEDs for turning on the capsule endoscope 3 before examination.

Figure 7:
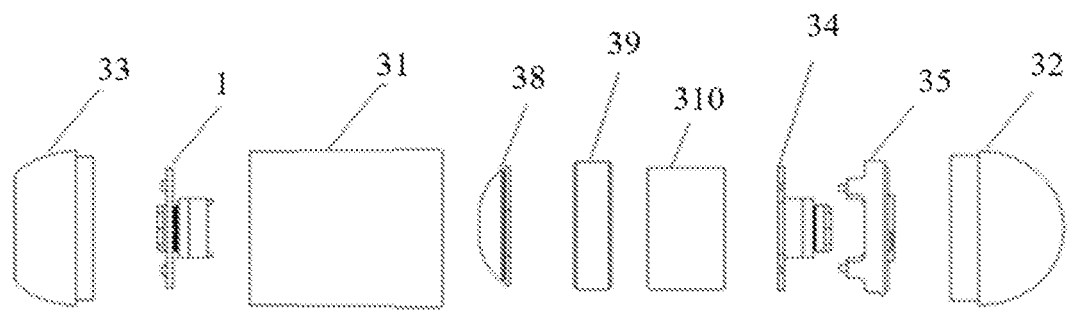
FIG. 7 shows an explored perspective view of the exemplary capsule endoscope of FIG. 2.

Referring to FIG. 7, the capsule endoscope 3 comprises the diagnostic imaging means 1 (OBM module) situated in the enclosed housing corresponding to the rear end 33, and the RF switch 38, battery 39 and magnet 310 enclosed in the housing corresponding to the capsule shell 31. The magnet 310 may be a permanent magnet dipole. The capsule endoscope 3 further comprises the photographic camera 34 disposed in the enclosed housing at a position corresponding to the front end 32. The photographic camera 34 can be integrated with the first light source 35. In the capsule endoscope 3, the rear end 33, the capsule shell 31 and the front end 32 have an interlock mechanism such that the capsule shell 31 can connect the rear end 33 and the front end 32 and securely lock them in place. In one example, the interlock mechanism is a male/female joint. In one instance, the rear end 33 and the front end 32 both have male joints, and both ends of the capsule shell 31 have female joints.

The front end 32 moves first as the capsule endoscope 3 navigates through the gastrointestinal tract of a patient, so the dome shaped front end 32 provides unique smooth and curved surface to help reduce friction, or even open up wrinkles of the walls of the gastrointestinal tract, while providing very minimal discomfort to the patient. Further the front end 32 is made of transparent materials. Further the front end 32 is made of materials transparent in 400-1200 nm wavelength. Optionally, the front end 32 further comprises an anti-reflective coating, to enhance the transmission of light source to improve the image quality by reducing the level of noise.

Similarly, the rear end 33 also requires a sphere surface to help the capsule 3 navigate through the gastrointestinal tract of a patient. However, when the diagnostic imaging means 1 employs an OBM module, the light sources need to be symmetric with respect to the center of the diagnostic imaging means 1, that is, the number of the second light source 36 and the third light source 37 is the same. At this time, light sources of different wavelengths can be used, that is, the second light source 36 and the third light source 37 can emit light of different wavelengths (for example, the second light source 36 emits red light, and the third light source 37 emits blue light or green light), and the second light source 36 and the third light source 37 are simultaneously lit up to provide illumination the diagnostic imaging means 1 for optical biopsy. In other embodiment, light sources of the same wavelength or the same spectrum are used, that is, the second light source 36 and the third light source 37 emit light of the same wavelength or light of the same spectrum (for example, white light), and the second light source 36 and the third light source 37 are separately lit up to provide illumination the diagnostic imaging means 1 for optical biopsy. In this embodiment, the second light source 36 and the third light source 37 are used to provide illumination having a wavelength of 0.2 to 300 μm.

In order to reduce the background noise due to the position of LEDs, the rear end 33 is preferably provided with a flat surface. Therefore, the sphere-shaped rear end is truncated to provide a flat face for OBM detection. Additionally, the flat face of the rear end 33 is made of light transparent materials. Optionally, the flat surface of the rear shell further comprises a variety of coatings, including but not limited to anti-reflective coatings.

The capsule endoscope 3, in accordance with the present invention, may optionally further comprise surface abrasion structures to enhance friction between capsule endoscope 3 and interior wall of the target area. Said surface abrasion structures may further help the capsule endoscope 3 to be anchored at the specific location or disposed in the specific orientation. Said abrasion structures include any type of rings and protrusions.

In one embodiment of the present invention, the capsule endoscope 3 can be placed close to either top wall or the bottom wall of the target area, where in the longitude direction of the at the liquid and gas interface within the target area. In another embodiment of the present invention, the capsule endoscope 3 can be floated or immersed in the liquid while taking the pictures or performing an optical biopsy.

In the scope of the present invention, in some examples, suspended horizontally means when a test subject lies down on a surface, and said surface is placed horizontally to the ground level, then the capsule endoscope 3 is suspended parallel to the ground level. In the scope of the present invention, in some examples, suspended horizontally means when the capsule endoscope 3 is placed in a target area, the target area has an interior wall which has a flat surface, and the capsule endoscope 3 is either suspended by liquid or supported by the surface abrasion structures thereon, to be in parallel to at least one interior wall of target area. Further, if the interior area does not have a surface which is flat, for example, when the capsule endoscope 3 examines the interior of a stomach, the capsule to be placed horizontally means, the length of the capsule is parallel to the tangent of the surface of a curved interior wall. In the scope of the present invention, in some examples, suspended vertically means when a test subject lies down on a surface, and said surface is placed horizontally to the ground level, then the capsule endoscope 3 is suspended vertically to the ground level. In the scope of the present invention, in some examples, the capsule endoscope 3 is supported vertically means when the capsule endoscope 3 is placed in a target area, the target area has an interior wall which has a flat surface, and the capsule endoscope 3 is supported by the surface abrasion structures thereon and perpendicular to the surface of the interior wall. In some examples, the capsule endoscope 3 is supported vertically means when the capsule endoscope 3 is placed in a target area, the target area has an interior wall which has a curved surface, and the capsule endoscope 3 is supported by the surface abrasion structures thereon and perpendicular to the tangent of the curved surface of the interior wall. In some examples, the capsule endoscope 3 is suspended vertically means when the capsule endoscope 3 is placed in a target area having a liquid, the capsule endoscope 3 is suspended at the liquid/gas interface vertically means the length direction of the capsule and liquid/gas interface form an angle around 90 degrees.

The capsule shell 31 of the capsule endoscope 3 is substantially cylindrical shaped. The magnet 310 is placed in the capsule shell 31 closer to the front end 32, so that the weight center is close to the magnetic center. In one example, the weight center and magnetic center is less than 2 mm to offer stable anchor under an external magnetic field. In a preferred example, the weight center and magnetic center is less than 1 mm.

The diameter of the front end 32 is the same as the diameter of the capsule shell 31, for example 12 mm. The rear end 33 has the truncated hemisphere with the diameter is 8 mm, for example.

The capsule endoscope 3 can further comprise a battery 39 to power the various functional modules. The battery 39 and the magnet 310 are heavier parts than others, therefore it is preferred to fix both the battery 39 and the magnet 310 in the approximate middle of the capsule shell 31.

Figure 8:
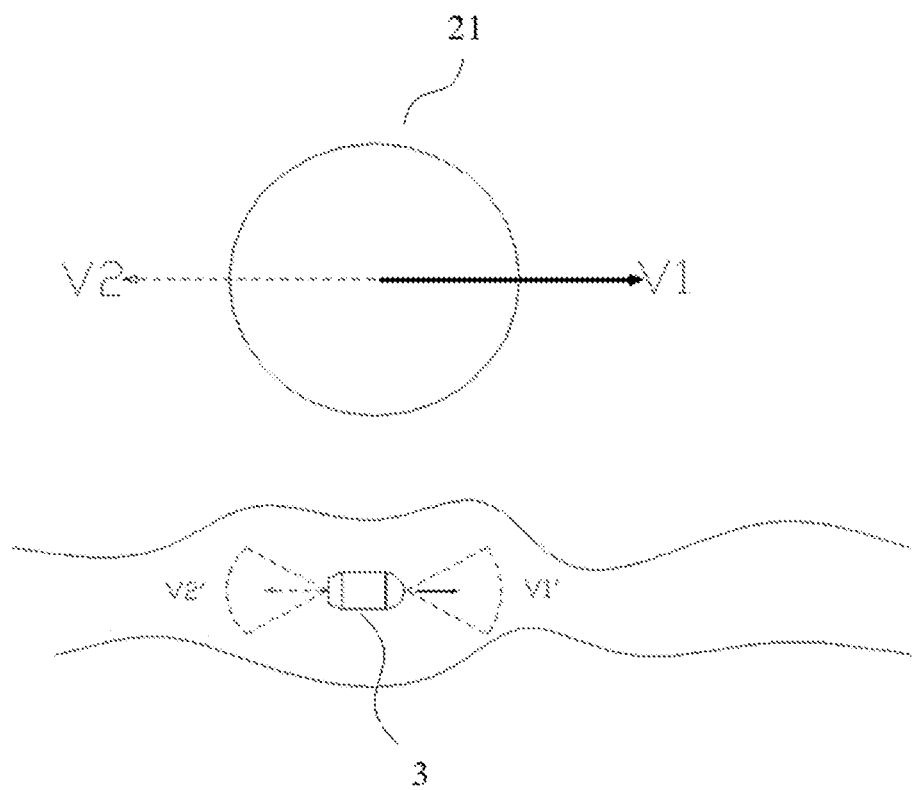
FIG. 8 shows a schematic illustration of an exemplary capsule endoscope in a floating state, wherein the capsule endoscope is suspended horizontally and said capsule endoscope can be moved forward and backward in accordance with the movement of the external magnetic ball.
Figure 9:
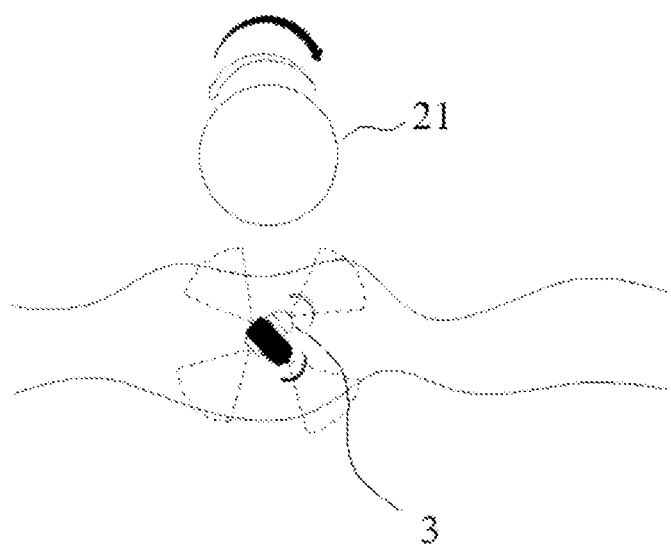
FIG. 9 shows a schematic illustration of an exemplary capsule endoscope floated in a liquid, wherein the capsule endoscope is suspended horizontally and the angle between the capsule endoscope and liquid can be adjusted in accordance with the rotational movement of the external magnetic ball.

The external control device 2 may comprise a magnetic ball 21 (referring to FIG. 8) and a controller (not shown) that interacts with the magnetic ball 21. The magnetic ball 21 is used to generate an external magnetic field to interact with the magnet 310 inside the capsule endoscope 3 to change the position and/or orientation of the capsule endoscope 3; the controller is configured for controlling the magnetic ball 21 to move, so as to control the diagnostic imaging means 1 to perform diagnostic imaging on the target area.

FIGS. 8-12 illustrates the basic method steps that how the capsule endoscope 3 having one photographic camera and one OBM camera travels in the gastrointestinal track. In one embodiment, the method comprises providing a capsule endoscope 3 having a permanent magnetic dipole placed in a target area, comprising a liquid/gas interface; and position an external magnetic ball 21 in close proximity to the capsule endoscope 3 so that the magnetic dipole inside the capsule endoscope 3 can changes its position and orientation in response to the movement and rotation of the external magnetic ball 21. Next, suspending the capsule endoscope 3 either at the liquid/gas interface or in the liquid by applying magnetic field force to the capsule endoscope 3 to balance the weight and floating force experience by the capsule endoscope 3. Preferably, the capsule endoscope 3 is suspended horizontally at the liquid/gas interface, having the front end facing the direction of movement. Then the capsule endoscope 3 can move forward and backward along the horizontal direction because of the lateral movement of the external magnetic ball 21.

Once the capsule endoscope 3, while being horizontally suspended, is guided into a target area of interest, the capsule endoscope 3 will be reoriented to change its pasture in order for the photographic camera 34 to scan the interior surface and take pictures. The method comprises the steps of flipping the capsule endoscope 3 from its horizontal position, and having the front photographic camera 34 pointing towards the area of interest, and identify a marker in the interior area to label its first position; changing its orientation and taking pictures as the capsule endoscope 3 rotates in accordance with the rotation and vertical movement of the external magnet ball 21.

Figure 10:
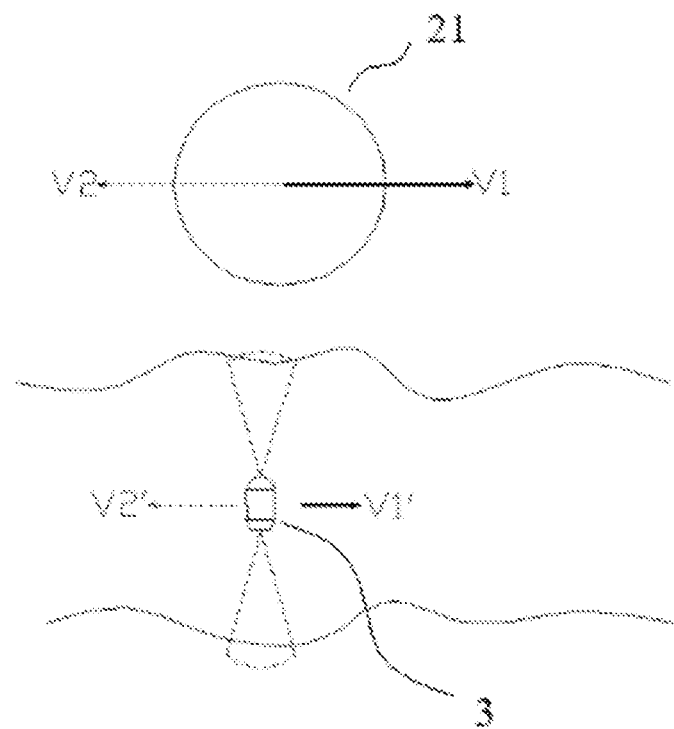
FIG. 10 shows a schematic illustration of an exemplary capsule endoscope in a floating state, wherein the capsule endoscope is suspended vertically and said capsule can be moved forward and backward in accordance with the movement of the external magnetic ball.

FIG. 10 schematically illustrates an alternative embodiment of FIG. of 8. In another embodiment, the method to navigate the capsule endoscope 3 having one photographic camera 34 and one diagnostic imaging means 1, comprises providing a capsule endoscope 3 having a permanent magnetic dipole placed in a target area, comprising a liquid/gas interface; and positioning an external magnetic ball 21 in close proximity to the capsule endoscope 3 so that the magnetic dipole inside the capsule endoscope 3 can change its position and orientation in response to the movement and rotation of the external magnetic ball 21. Next, suspending the capsule endoscope 3 at the liquid/gas interface by applying magnetic field force to the capsule endoscope 3 by balancing the weight and floating force experience by the capsule endoscope 3, wherein the capsule endoscope 3 is suspended vertically at the liquid/gas interface. Then moving the capsule endoscope 3 to the left or right direction by the lateral movement of the external magnetic ball 21, wherein the left and right direction is not parallel to but perpendicular to the length direction of the capsule endoscope 3, and the left and right direction movement of the capsule endoscope 3 allows the front end of the capsule endoscope 3 facing an exposed interior wall of the target area. Further the photographic camera 34 takes pictures when the capsule endoscope 3 travels laterally along the liquid/gas interface.

FIG. 10 describes a method of scanning the interior surface of the target area by moving the capsule endoscope 3. Alternatively, scanning an interior surface of the target area can also be performed by anchoring the capsule 3 at a desired position and scan the surface above it by changing its orientation. When the capsule endoscope 3 disclosed in the present invention vertically suspended at the gas/liquid interface, having the front shell positioned above the gas/liquid interface, the capsule endoscope 3 can either swing from left to right to scan a slice of the surface above it, or evolve around its anchor position to scan a broader surface of the interior surface. In one embodiment of the present invention, the method to navigate the capsule endoscope 3 having one photographic camera 34 and one diagnostic imaging means 1, comprises providing a capsule endoscope 3 having a permanent magnetic dipole placed in a target area, comprising a liquid/gas interface; and positioning an external magnetic ball 21 in close proximity to the capsule endoscope 3 so that the magnetic dipole inside the capsule endoscope 3 can change its position and orientation in response to the movement and rotation of the external magnetic ball 21. Next, suspending the capsule endoscope 3 at a first position at the liquid/gas interface and forming a first tilt angle between the length of the capsule endoscope 3 and gas/liquid interface by applying magnetic field force to the capsule endoscope 3; rotating the capsule endoscope 3 to either left and right, changing its title angle formed between its length and the gas/liquid interface while being anchored at the first position at the gas/liquid interface, and taking images by the photographic camera 34 by the front end of the capsule endoscope 3.

Figure 12:
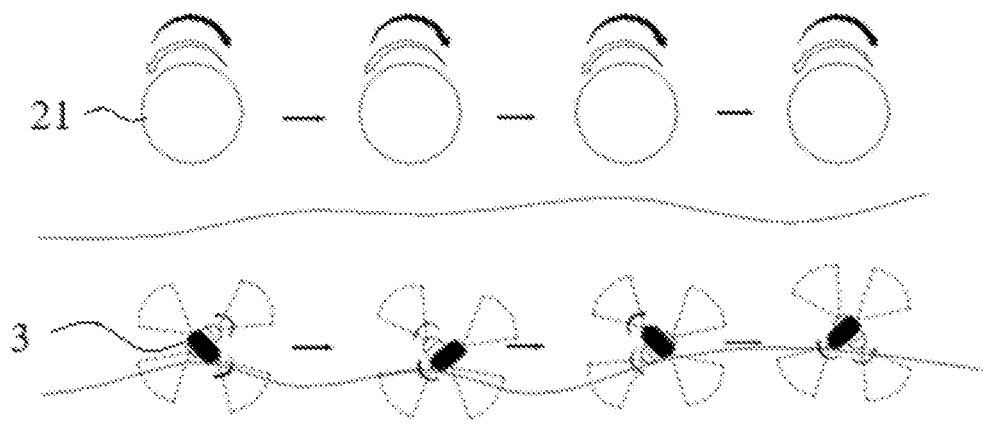
FIG. 12 shows a schematic illustration of an exemplary capsule endoscope located on the wall of colon, wherein the capsule endoscope can rotate continuously to scan the interior of the target area.

FIG. 12, illustrates that the capsule endoscope 3 can scroll continuously while moving forward in a linear manner, under the influence of the external magnetic field. The capsule endoscope 3 can flip when it at the top or bottom.

Figure 11:
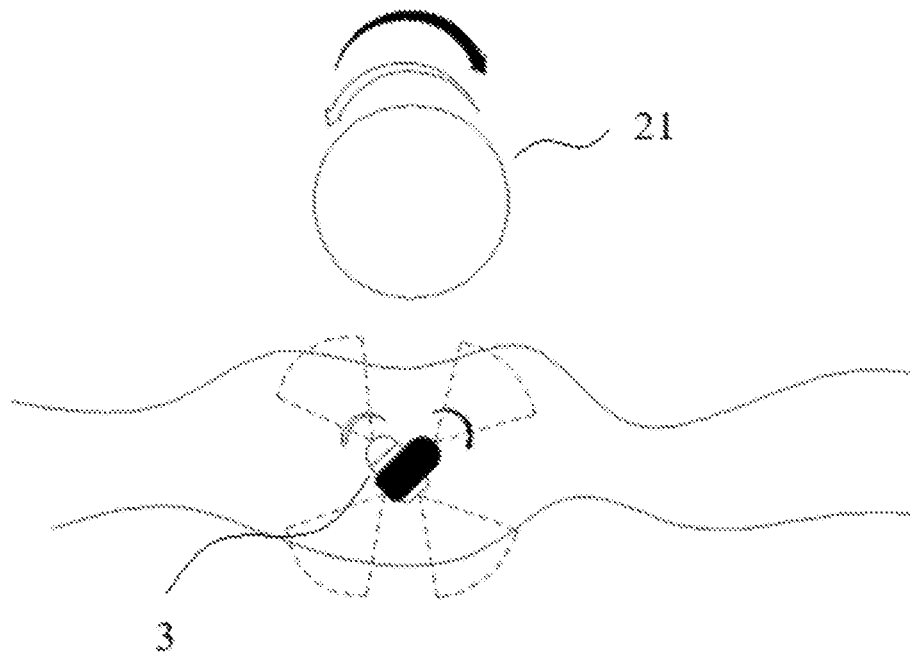
FIG. 11 shows a schematic illustration of an exemplary capsule endoscope floated in a liquid, wherein the capsule endoscope is suspended vertically and the angle between the capsule endoscope and liquid can be adjusted in accordance with the rotational movement of the external magnetic ball.

Referring to FIGS. 10, 11, 13a and 13b, when the capsule endoscope 3 is introduced into a target area, the capsule endoscope 3 is suspended in a way that the front end bearing the photographic camera 34 is above the gas/liquid interface. The photographic camera 34 can take a first picture and rotate from left to right as shown in FIG. 11 or moving up or down with respect to the gas/liquid interface to the interior surface as desired by moving the external magnetic ball 21 vertically or adjusting the vertical distance between the external magnetic ball 21 and capsule endoscope 3. Optionally, under some usual circumstances, it is desired to immerse the front end of the capsule endoscope 3 to be underneath the liquid/gas interface. Similarly, the capsule endoscope 3 can move up and down in accordance with the vertical movement of the external magnetic ball 21.

FIGS. 8-12, describe when a capsule endoscope 3 is introduce into a target area filled with a gas and liquid, and capsule is navigated in the target area while being suspended. FIGS. 13a-17 describe when a capsule endoscope 3 is introduced into a target area, wherein the target area has been previously vacated and filled with a gas, for example air.

Figure 13A:
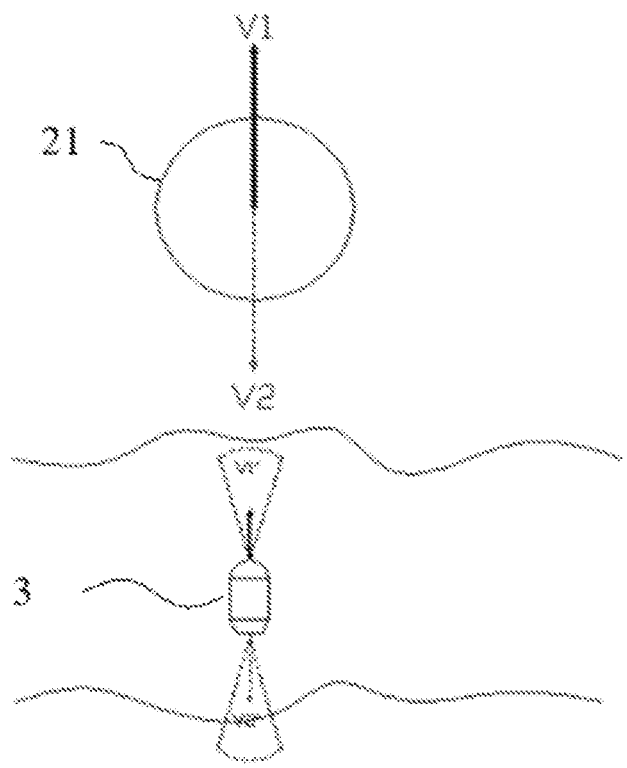
FIG. 13a shows a schematic illustration of an exemplary capsule endoscope floated in a liquid, wherein the front end of the capsule endoscope faces towards the magnetic ball and the capsule endoscope can move up and down vertically in response to the movement of the external magnetic ball.
Figure 13B:
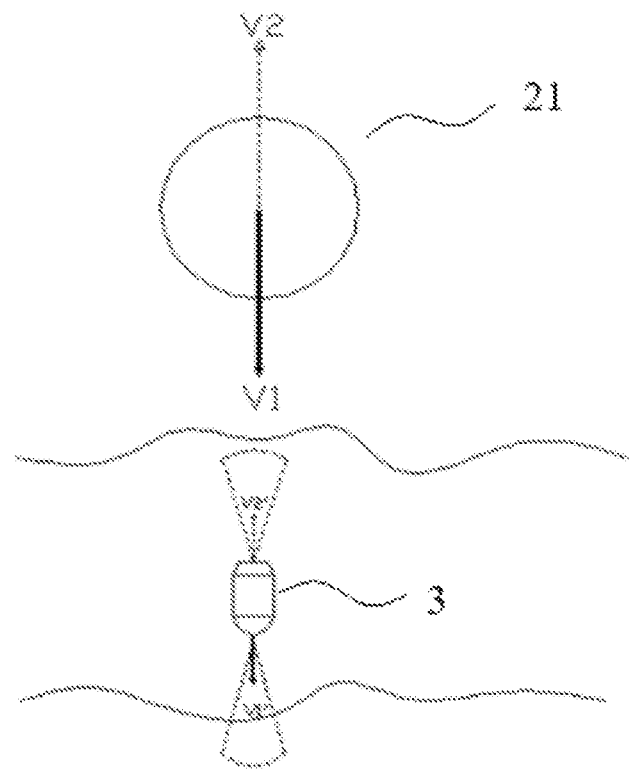
FIG. 13b shows a schematic illustration of an exemplary capsule endoscope floated in a liquid, wherein the rear end of the capsule endoscope faces towards the magnetic ball and the capsule endoscope can move up and down vertically in response to the movement of the external magnetic ball.
Figure 14A:
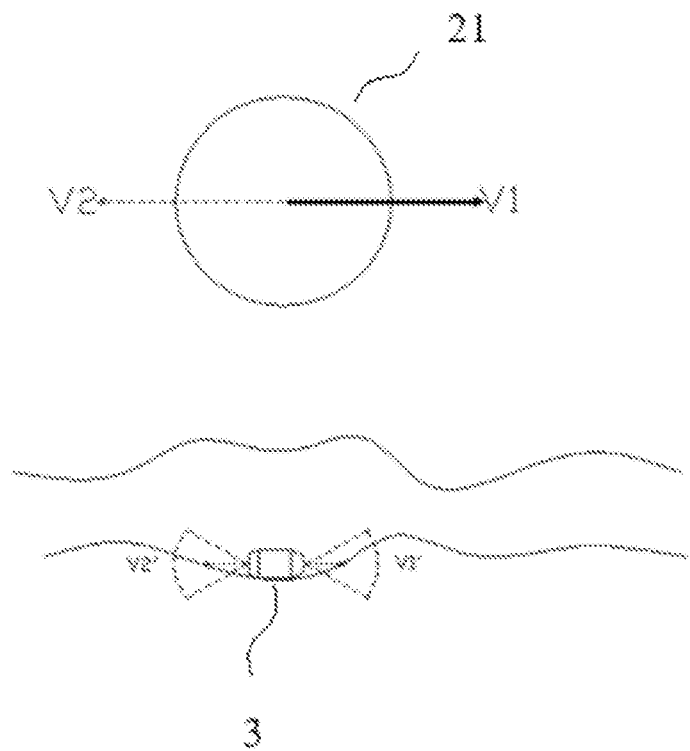
FIG. 14a shows a schematic illustration of an exemplary capsule endoscope in a target area, wherein the capsule endoscope can move along a first surface of the target area and scan the first surface.

Referring to FIGS. 13a and 13b, and FIGS. 14a and 14b, when the capsule endoscope 3 is introduced into a target area filled with air, the capsule endoscope 3 can either be suspended in the air (FIGS. 13a and b) or be placed next to a surface of the interior wall of the target area (FIGS. 14a and b). As illustrated in FIGS. 13a and 13b, the capsule endoscope 3 will adopt an upright position with respect to either a first or second surface, having the front end facing either a first or second surface of the capsule endoscope 3. Then the capsule endoscope 3 can be moved either closer or farther away towards the first or second surface, while the photographic camera 34 can take pictures simultaneously. In one embodiment of the present invention, the method to place the capsule endoscope 3 having one photographic camera 34 and one diagnostic imaging means 1, comprises providing a capsule endoscope 3 having a permanent magnetic dipole placed in a target area filled with a gas; and positioning an external magnetic ball 21 in close proximity to the capsule endoscope 3 so that the magnetic dipole inside the capsule endoscope 3 can change its position and orientation in response to the movement and rotation of the external magnetic ball 21. Next, applying magnetic field force to the capsule endoscope 3 to suspend the capsule endoscope 3 at a upright position with respect to a first surface of the target area, having the front end bearing the photographic camera 34 pointing toward the first surface; repositioning the capsule endoscope 3 to be either closer and father away from the first surface and taking images by the photographic camera 34 simultaneously by adjusting the distance between the external magnetic ball 21 and the first surface of the target area.

Figure 14B:
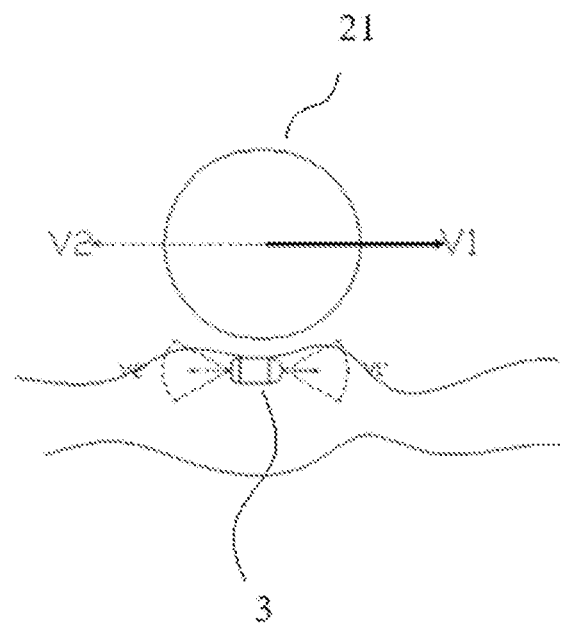
FIG. 14b shows a schematic illustration of an exemplary capsule endoscope in a target area, wherein the capsule endoscope can move along a second surface of the target area.

As illustrated in FIGS. 14a and 14b, the capsule endoscope 3 is placed in direct contact on a surface of the target area, which is filled with a gas, having the front end facing either a first or second surface of the capsule endoscope 3. Then the capsule endoscope 3 can be moved forward or backward along the first or second surface by moving the external magnetic ball 21 along the direction of the first or second surface, while the photographic camera 34 can take pictures simultaneously.

Figure 15:
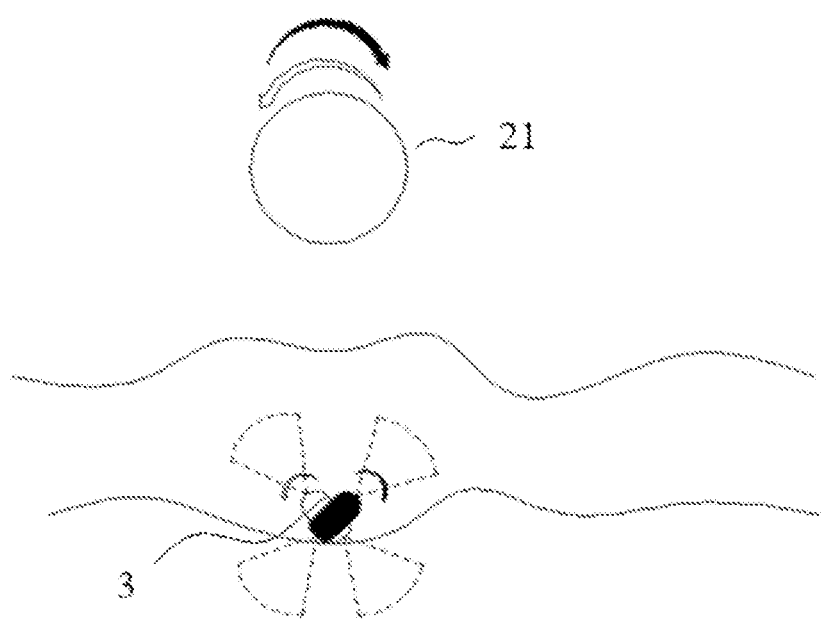
FIG. 15 shows a schematic illustration of an exemplary capsule endoscope in a target area, wherein the capsule endoscope can move along the first surface of the target area, capsule endoscope forming a tilt angle with the first surface and capsule endoscope scan the second surface.
Figure 16:
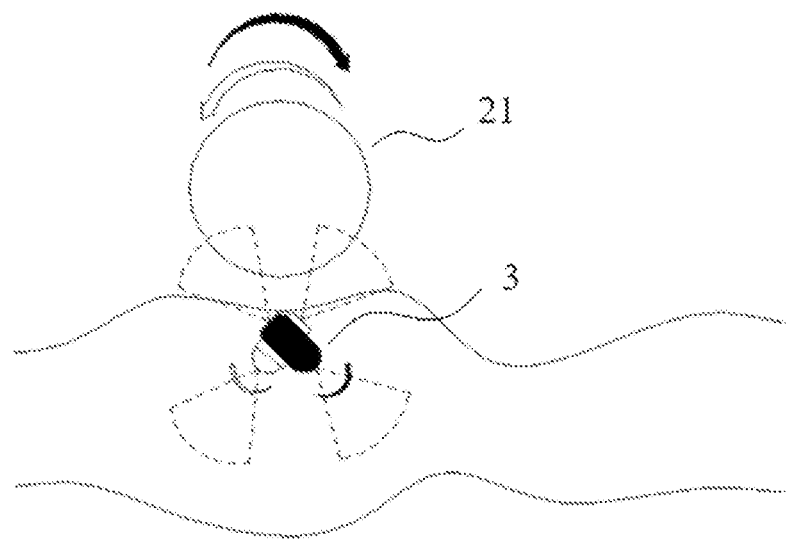
FIG. 16 shows a schematic illustration of an exemplary capsule endoscope in a target area, wherein the capsule endoscope can move along the second surface of the target area, capsule endoscope forming a title angle with the second surface and capsule endoscope scan the first surface, wherein the second surface is closer to the external magnetic ball than the first surface.
Figure 17:
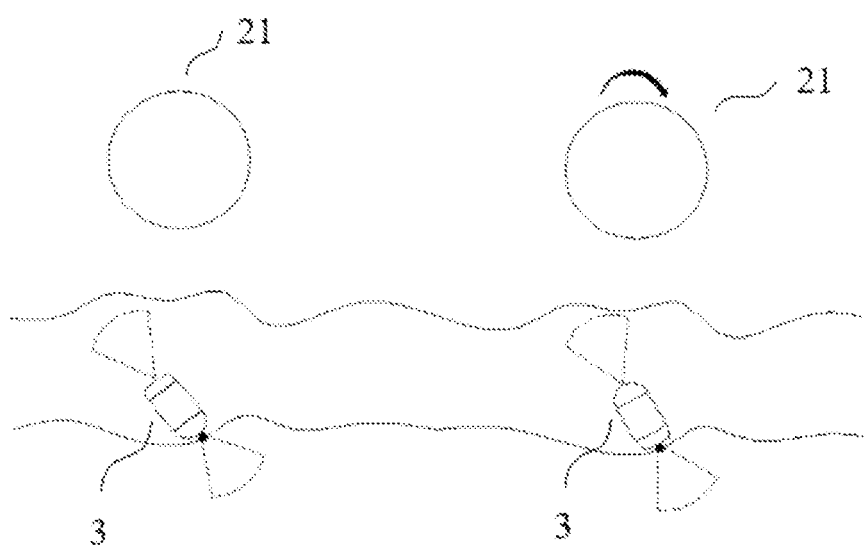
FIG. 17 shows a schematic illustration of an exemplary capsule endoscope in a target area, wherein the capsule endoscope changes its orientation from having the camera pointing to the diseased area.
Figure 18:
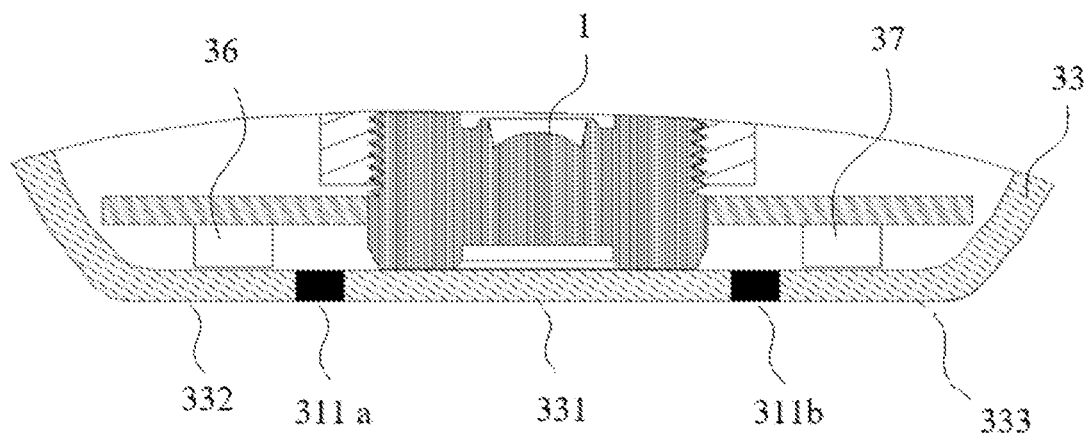
FIG. 18 shows a cross sectional view of the truncated hemisphere end of the capsule endoscope.
Figure 19:
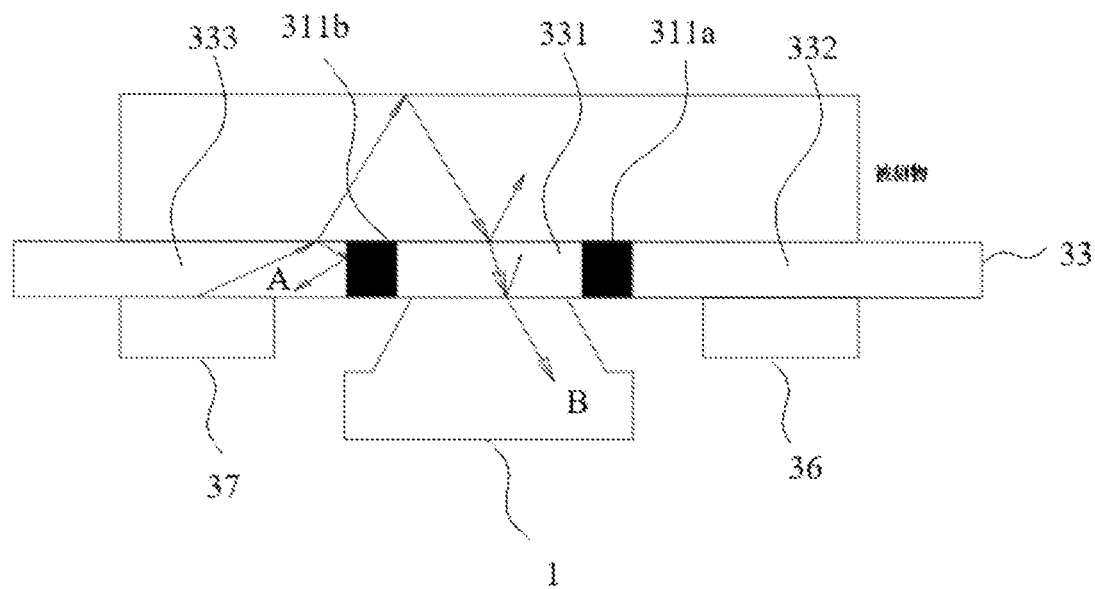
FIG. 19 shows a schematic view showing a structure in which the rear end is provided with a light blocking ring.
Figure 20:
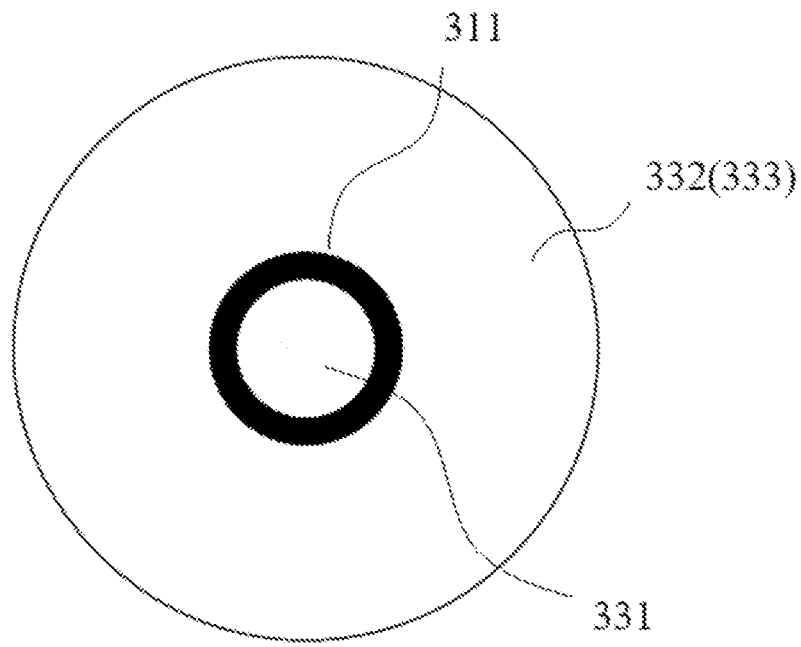
FIG. 20 shows a bottom view of FIG. 18.
Figure 21:
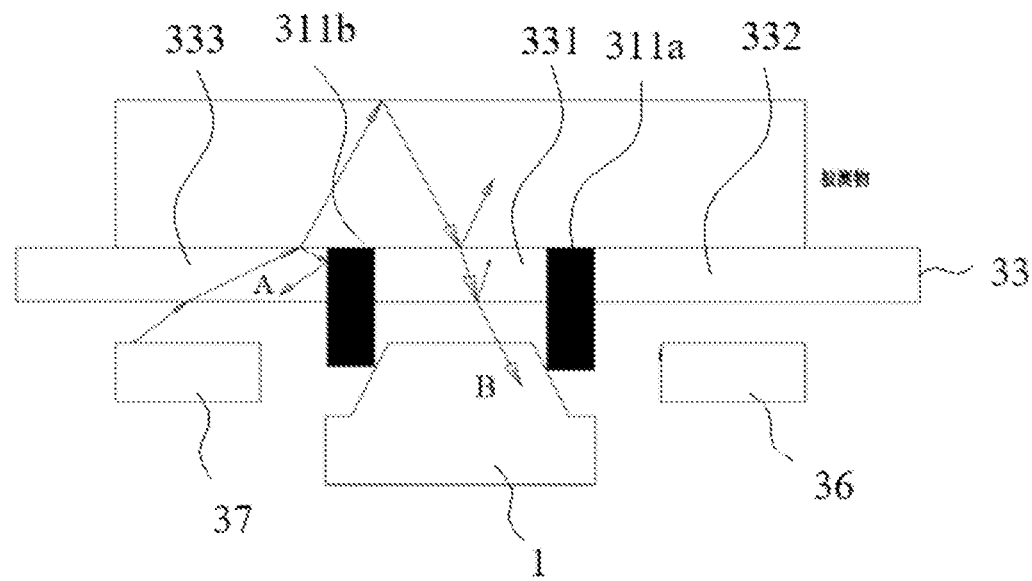
FIG. 21 shows a schematic view showing another structure in which the rear end is provided with a light blocking ring.

While as the capsule endoscope 3 moves along a first surface, the front end thereof can be further lifted up and rotate to scan the images of the surface opposing to the first surface as shown in FIGS. 15 and 16. As illustrated in FIG. 15, when the capsule endoscope 3 having one photographic camera 34 and one diagnostic imaging means 1 is placed in a target area filled with a gas, for example, air or $CO_2$, the capsule endoscope 3 will automatically rest and by supported by a first surface of the target area with/without the external magnetic field because of the weight of the capsule endoscope 3. Next, rotating and moving the external magnetic ball 21, to lift up the front end of the capsule endoscope 3 to take pictures. FIG. 16, shows a follow-up method step to examine the opposing surface of the first surface. The capsule endoscope 3 is hang up on a second surface with is opposite to the first surface having the front end pointing downwards and towards to the first surface, scanning the images of the first surface. In one embodiment of the present invention, the method comprising providing the capsule endoscope 3 having a permanent magnetic dipole; guiding the capsule endoscope 3 into a target area filled with a gas by applying external magnetic field and placing the capsule endoscope 3 as rested on a first surface; lifting the front end of the capsule endoscope 3 up towards a second surface and scanning the second surface by applying rotational magnetic field and taking pictures of the second surface by the photographic camera 34 housed in the front end of the capsule endoscope. Then dislocating the capsule endoscope 3 from the first surface and moving the capsule endoscope 3 to the surface, hang it upside down while the front end facing toward the first surface by moving the external magnetic ball 21 closer to the second surface, and scanning the surface of the first surface.

In accordance with the aspects of the present invention, the capsule endoscope 3 having both the photographic camera 34 for scanning and a diagnostic imaging means 1 for biopsy, is always using the photographic camera 34 to collect picture data first to decide there is a diseased region which needs further examination. Once the diseased region is determined, the capsule endoscope 3 can be flipped or rotated 180 degrees, to have the diagnostic imaging means 1 facing towards the diseased region and performing an optical biopsy.

FIGS. 8-17 listed fundamental method steps in using the capsule endoscope 3 having both a photographic camera 34 and a diagnostic imaging means 1. Each method steps as illustrated in meant to be used in conjunction with other method steps to be effectively exam and diagnose a target area. In one embodiment of the present invention, the diagnostic imaging means 1 is OBM (Oblique back-illumination microscopy). In another embodiment of the present invention, the diagnostic imaging means 1 is SECM (Spectrally-encoded confocal microscopy).

In one embodiment of the present invention, the capsule endoscope 3 comprises a first light source 35 for the photographic camera 35 at the front end, a second light source 36 and a third light source 37 for diagnostic imaging means 1 at the rear end of the capsule endoscope 3. Where in the first light source 35, the second light source 36 and the third light source 37 can be one or more LEDs; and the second light source 36 and the third light source 37 are the same in quantity and are symmetrically disposed around the diagnostic imaging means 1. When the second light source 36 and the third light source 37 emit light of different wavelengths, the second light source 36 and the third light source 37 are simultaneously lit up to provide illumination the diagnostic imaging means 1 for optical biopsy; when the second light source 36 and the third light source 37 emit light of the same wavelength, the second light source 36 and the third light source 37 are separately lit up to provide illumination the diagnostic imaging means 1 for optical biopsy. In one example the first light source 35 includes two white LEDs, which are identical and produce lights in the visible light region. In another example, the second light source 36 and the third light source 37 are six LEDs, surrounding the camera of the diagnostic imaging means 1. In one instance, three of the LEDs are identical and emitting light at a first wavelength, and three of the LEDs are identical and emitting light at a second wavelength, and the first and second wavelength are different and distinguishable. In another instance, the first three LEDs are red emitting LEDs and other three LEDs are blue LEDs. In another example, once a diseased region is determined, the LEDs are configured for illumination of the diseased region by the second and third light sources with orthogonally polarized light.

In one embodiment, the first light source 35 and the second light source 36 are capable of providing illumination at a range of wavelengths comprising from 0.2 to 300 um.

In another embodiment, the first light source 35, the second light source 36 and the third light source 37 are selected from a light-emitting diode (LED), a laser, a supercontinuum light source, or a superluminescent diode (SLED).

In further embodiment of the present invention, corresponding the position of the diagnostic imaging means 1, the front end 32 or the rear end 33 of the capsule endoscope 3 further comprises a transparent surface and a non-transparent surface. In this example, the diagnostic imaging means 1 corresponds to the rear end 33, the non-transparent surface is placed between the surface next to the LED (the second light source 36 or the third light source 37) and the surface next to the OBM lens, wherein any non-transparent surface is placed in between transparent surfaces. The non-transparent surface is placed to prevent the stray light of LED from received by the OBM lens, which may cause disturbance to imaging result of the target area (for example, image blur and contrast reduction).

As illustrated from FIG. 18 to FIG. 21, a first light blocking part 311a is configured between the first area 331 at the front end 32 or the rear end 33 corresponding to the diagnostic imaging means 1 and the second area 332 at the front end 32 or the rear end 33 corresponding to the second light source 36. A second light blocking part 311b is configured between the first area 331 at the front end 32 or the rear end 33 corresponding to the diagnostic imaging means 1 and the third area 333 at the front end 32 or the rear end 33 corresponding to the third light source 37.

The first light blocking part 311a and the second light blocking part 311b may be provided separately or integrated on the same light blocking ring 311. The light blocking ring 311 is disposed around the lens of the OBM module. Since the light emitted by the LED is divided into two parts, the emitted and the reflected light, passing through the rear end 33. The emitted light is reflected back to the rear end 33 after entering the object to be tested, and the beam B entering the lens of the OBM module after the rear end 33 is effective light. Part of the reflected light enters the lens of the OBM module, which is stray light A. After the light blocking ring 311 is disposed, the reflected light blocked by the light blocking ring 311 is emitted to other places, and does not enter the lens of the OBM module, thereby preventing stray light from interfering with the imaging result of the lens.

The light blocking ring 311 can be embedded in the rear end 33, with the height same as the material thickness of the rear end 33, or the height of the light blocking ring 311 can be set higher than the material thickness of the rear end 33, so that extending the light blocking ring 311 close to the LED to the inner surface of the rear end 33. One side of the light blocking ring 311 protrudes from the inner surface of the rear end 33, and can be set by a person skilled in the art according to actual conditions.

The capsule endoscope 3 may also include, but is not limited to, a CMOS, a 3D magnetic sensor, a 3D gyro sensor, a CPU, and an ASIC image processor.

After the capsule endoscope 3 turns on, all the functions of photographic camera 34 and the diagnostic imaging means 1 can be individually controlled by the CPU and/or ASIC/FPGA inside the capsule endoscope 3. The images obtained by the photographic camera 34 or OBM module are processed by the ASIC/FPGA module, the timing of taking the images is controlled by CPU. The CPU can read the values of sensors and all that information can be used to calculate the capsule special location, wherein the sensors include all sensors in FIG. 19. The capsule functions can be controlled by the commands that received from the RF module inside the capsule endoscope 3. The RF signal can be either 2.4 GHz or 433 Mhz or other frequencies. The external control device 2 comprises a controller which is used to communicate with the capsule endoscope 3, receiving imaging and sensor data as well as sending commands to the capsule endoscope 3. The controller can also communicate with PC, PAD or smart phone by USB, Ethernet, Bluetooth, WiFi or other ways to display the image on the screen in real-time.

An endoscopic imaging system operating in a controller of the external control device 2 for controlling the capsule endoscope 3 is disclosed in the present invention. The controller comprises a processing unit and a memory, and the memory comprises at least one type of readable storage medium. The readable storage medium may be a non-volatile storage medium such as a flash memory, a hard disk, a multimedia card, a card type memory, or the like. The processing unit may be a central processing unit (CPU), a microprocessor or other data processing chip for running program code or processing data stored in the memory, such as executing the program code of the endoscopic imaging system.

The endoscopic imaging system controls the capsule endoscope 3 in the steps as follows: obtain the position of the capsule endoscope 3 and control the capsule endoscope 3 to move to the target area; control the capsule endoscope 3 to change orientation; control the diagnostic imaging apparatus 1 to perform diagnostic imaging on the target area.

The endoscopic imaging system can also control the capsule endoscope 3 in the steps as follows: obtain the position of the capsule endoscope 3 and control the capsule endoscope 3 to move to the target area; control the photographic camera 34 to the target area to take pictures and/or record videos; control the capsule endoscope 3 to change orientation; and control the diagnostic imaging apparatus 1 to perform diagnostic imaging on the target area.

The endoscopic imaging system can also control the capsule endoscope 3 in the steps as follows: obtain the position of the capsule endoscope 3 and control the capsule endoscope 3 to move to the target area; control the photographic camera 34 to the target area to take pictures and/or record videos; control the magnetic ball 21 of the external control device 2 to rotate the capsule endoscope 3 by 180 degrees; control the second light source 36 and the third light source 37 to illuminate the target area; and control the diagnostic imaging apparatus 1 to perform diagnostic imaging on the target area.

Figure 22:
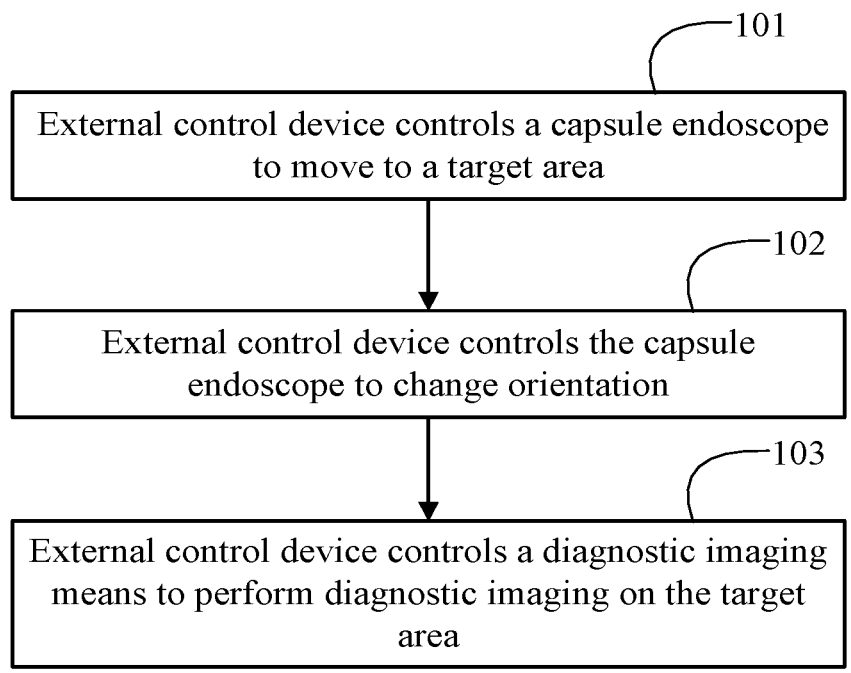
FIG. 22 shows a flowchart of a front endoscopic imaging method according to an embodiment of the present invention.

As illustrated in FIG. 22, the present invention also discloses an endoscopic imaging method, comprising:

S101, the external control device 2 controls the capsule endoscope 3 to move to a target area;

S102, the external control device 2 controls the capsule endoscope 3 to change orientation;

S103, the external control device 2 controls the diagnostic imaging means 1 to perform diagnostic imaging on the target area.

The step S101 specifically comprises:

the magnetic ball 21 acts on the magnet 310 in the capsule 3 to control the capsule 3 to move to the target area.

Figure 23:
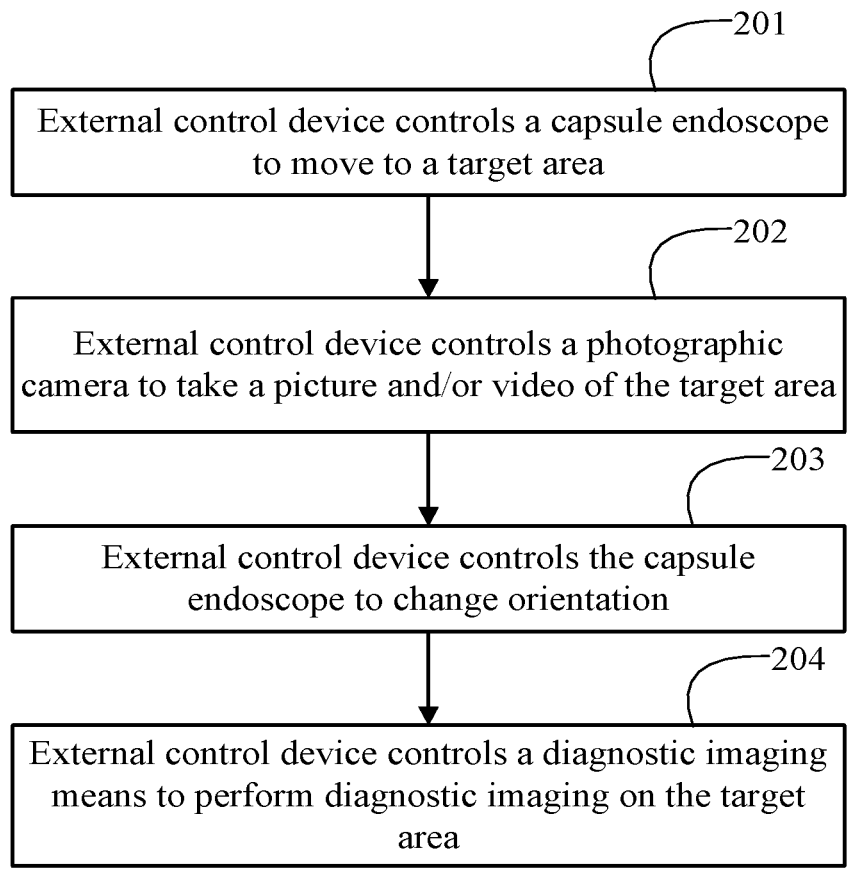
FIG. 23 shows a flowchart of a rear endoscopic imaging method according to an embodiment of the present invention.

As illustrated in FIG. 23, the methods in the embodiment comprising:

S201, the external control device 2 controls the capsule endoscope 3 to move to a target area;

S202, the external control device 2 controls the photographic camera 34 to take a picture and/or video of the target area;

S203, the external control device 2 controls the capsule endoscope 3 to change orientation;

S204, the external control device 2 controls the diagnostic imaging means 1 to perform diagnostic imaging on the target area.

Figure 24:
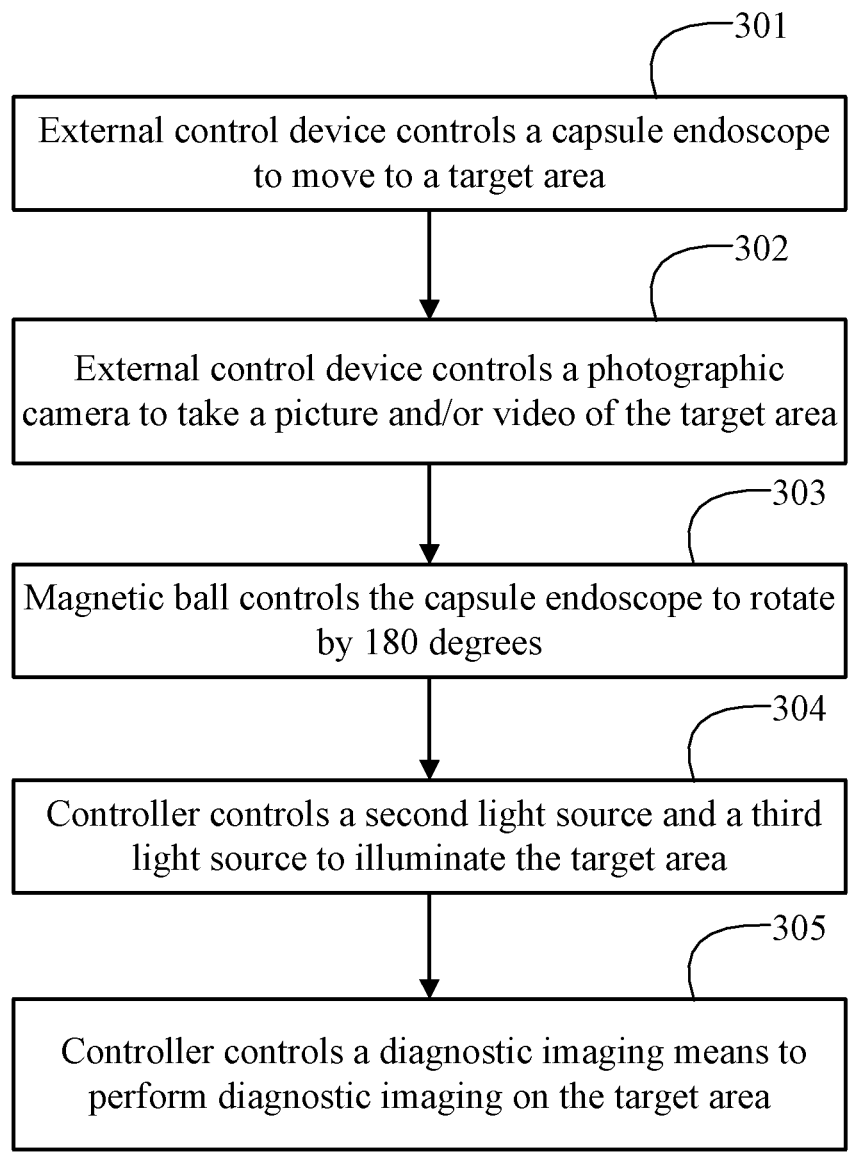
FIG. 24 shows a flowchart of a third endoscopic imaging method according to an embodiment of the present invention.

As illustrated in FIG. 24, the methods in this embodiment comprising:

S301, the external control device 2 controls the capsule endoscope 3 to move to a target area;

S302, the external control device 2 controls the photographic camera 34 to take a picture and/or video of the target area;

S303, the magnetic ball 21 controls the capsule endoscope 3 to rotate by 180 degrees.

S304, the controller controls the second light source 36 and the third light source 37 to illuminate the target area;

S305, the controller controls the diagnostic imaging means 1 to perform diagnostic imaging on the target area.

Before the examination, prepare a patient's stomach empty and ready for examination. A capsule endoscope 3 having a permanent magnetic dipole is placed in situ in the patient, and the capsule endoscope 3 position to a target area. The target area of a sample is illuminated with a first light source 35 to provide a photographic image, and the capsule endoscope 3 rotates for 180 degrees so that the first light source 35 points away from the sample when the same is decided to be a GI pathology. The target area of a sample is illuminated with a second light source 36 and a third light source 37 to provide a oblique back illumination of the target region of the sample and a phase contrast image is detected by using light originating from the second and third light source.

The method further comprises forming a direct contact between the capsule endoscope 3 and the sample by using the external magnetic ball 21 to obtain an OBM image.

Further, the step of illuminating the target area of a sample with a first light source 35 to provide a photographic image, further comprises scanning fundus of the patient to check both a ceiling and bottom wall thereof, then scanning the cardiac; scanning multiple regions of the patient's GI track including a pylorus, and scanning tantrum.

The aforementioned embodiments describe the system and method for an endoscopic imaging apparatus comprising a wireless capsule endoscope, wherein one photographic camera is on one end and the diagnostic imagining means is on the other end. In accordance with another aspects of the present invention, the endoscopic imaging apparatus can also comprise a tethered capsule endoscope having both the photographic camera and the diagnostic imaging means on the front end, as the embodiments listed below.

The invention claimed is:

1. An endoscopic imaging apparatus, comprising:
    a diagnostic imaging means,
    an external control device, and
    an ingestible capsule endoscope,
    wherein
    the external control device is configured to position and orientate the capsule in a target area;
    the diagnostic imaging means is included in the capsule endoscope for diagnostic imaging of a target area under the control of the external control device,
    the ingestible capsule endoscope
        having a front end and rear end, respectively fixed at two ends of an elongated capsule shell, and the front end, the rear end and the elongated capsule shell construct an enclosed housing, wherein the rear end has a flat surface configured to be placed next to the target area for diagnostic imaging;
        said capsule endoscope comprising
        a magnet, and the magnet and the diagnostic imaging means are included in the enclosed housing and work in conjunction with the external control device,
        the rear end of the housing is provided with a light transparent surface;
        a photographic camera, configured, in the enclosed housing, to take image and/or record video of the target area;
        a first light source for illumination of the target area, configured to work with the photographic camera or the diagnostic imaging means;
        a second light source and/or a third light source for illumination of the target area, configured for working with the diagnostic imaging means or the photographic camera; wherein the second and third light source surround the diagnostic imaging means which is next to an interior surface of the flat surface of the rear end;
        a first light blocking part, positioned between a first area of the rear end facing the diagnostic imaging means and a second area at the rear end facing the second light source; and
        a second light blocking part, positioned between the first area at the rear end corresponding to the diagnostic imaging means and a third area at the rear end facing to the third light source,
        wherein thickness of the first light blocking part and second light blocking part is equal to or greater than a thickness of the flat surface of the rear end.

2. The endoscopic imaging apparatus of claim 1, wherein the first light blocking part and the second light blocking part are on the same light blocking ring.

3. The endoscopic imaging apparatus of claim 1, wherein the second light source and the third light source are of the same quantity and are symmetric with respect to the center of the diagnostic imaging means.

4. The endoscopic imaging apparatus of claim 3, wherein the second and third light sources are capable of providing illumination at a range of wavelengths comprising from 0.2 to 300 um.

5. The endoscopic imaging apparatus of claim 1, wherein the second light source and the third light source are on the same side of the capsule endoscope; and the first light source is on a side of the capsule endoscope away from the second light source and the third light source.

6. The endoscopic imaging apparatus of claim 1, wherein the diagnostic imaging means is oblique back illumination microscopy.

7. The endoscopic imaging apparatus of claim 6, wherein the second source and the third source are used to simultaneously illuminate the diagnostic imaging means with light of the same wavelength or light of the same spectrum, or to separately illuminate the diagnostic imaging means with light of different wavelengths.

8. The endoscopic imaging apparatus of claim 1, wherein the external control device comprises a magnetic ball and a controller that is in conjunction with the magnetic ball;
    the magnetic ball acts on the magnet in the capsule to change the position and/or orientation of the capsule;
    the controller controls the diagnostic imaging means to perform diagnostic imaging on the target area.

* * * * *